(12) United States Patent
Bompeix et al.

(10) Patent No.: US 8,790,716 B2
(45) Date of Patent: Jul. 29, 2014

(54) PROCESS FOR TREATING STORAGE RESERVOIRS CONTAMINATED WITH MYCOTOXINS

(75) Inventors: Gilbert Bompeix, Paris (FR); Alberto Sardo, Chateaurenard (FR)

(73) Assignee: Xeda International, Saint Andiol (FR)

( * ) Notice: Subject to any disclaimer, the term of this patent is extended or adjusted under 35 U.S.C. 154(b) by 811 days.

(21) Appl. No.: 11/790,610

(22) Filed: Apr. 26, 2007

(65) Prior Publication Data

US 2008/0175926 A1 Jul. 24, 2008

(30) Foreign Application Priority Data

Apr. 27, 2006 (FR) ...................................... 06 03794

(51) Int. Cl.
*A61K 36/00* (2006.01)
(52) U.S. Cl.
USPC ......................................................... 424/725
(58) Field of Classification Search
None
See application file for complete search history.

(56) References Cited

U.S. PATENT DOCUMENTS 6,723,364 B1 * 4/2004 Bompeix et al. ............. 426/320

FOREIGN PATENT DOCUMENTS

FR 2 786 664 6/2000

OTHER PUBLICATIONS

Odhave et al., Incidence and biocontrol or some mycotoxins in South Africa, Bulletin OILB/SROP, 24 (3): 133-136, 2001.*
Jugal et al., Spice oils for the control of co-occurring mycotoxin-producing fungi, Journal of Food Protection, (Apr. 2002) vol. 65, No. 4, pp. 683-687.*
Olsen et al, Prevention strategies for ochratoxins in grain, Aspects of applied biology (2003) No. 68: 29-33.*
Odhav et al, Incidence and biocontrol or some mycotoxins in South Africa, Bulletin OILB/SROP, 24 (3): 133-136, 2001.*
Jugal et al, Spice oils for the control of co-occurring mycotoxin-producing fungi, Journal of Food Protection, (Apr. 2002) vol. 65, No. 4, pp. 683-687.*
McDonough et al, *Sporothrix* (*Sporotrichum*) *schenckii* in a nursery barn containing *Sphagnum*, Control of fungus with a disinfectant, 85 (7): 1970.*
N. N. Tripathi et al., "Toxicity of Some Terpenoids Against Fungi Infesting Fruits and Seeds of *Capsicum annuum* L. During Storage", Phytopatologische Zeitschrift, Verlag Paul Parey, Berlin, DE, vol. 110, pp. 328-335, XP002233030, ISSN: 0031-9481, 1984.
S. Juglal et al., "Spice Oils for the Control of Co-Occurring Mycotoxin-Producing Fungi", Journal of Food Protection, vol. 65, No. 4, pp. 683-687, XP009077641, 2002.
R. Montes-Belmont et al., "Control of *Aspergillus flavus* in Maize with Plant Essential Oils and Their Components", Journal of Food Protection, vol. 61, No. 5, pp. 616-619, XP000886016, ISSN; 0362-028X, May 1998.
Nada Mansour et al., "Inhibition of Surface Growth of Toxigenic and Nontoxigenic *Aspergilli* and *Penicillia* by Eugenol, Isoeugenol and Monolaurin", Journal of Food Safety, vol. 16, No. 3, pp. 219-229, XP009077671, 1996.

* cited by examiner

*Primary Examiner* — Qiuwen Mi
(74) *Attorney, Agent, or Firm* — B. Aaron Schulman, Esq.; Stites & Harbison, PLLC.

(57) ABSTRACT

A process for treating, by means of eugenol or clove oil, reservoirs for storing cereals, oil-producing plants, dry fruit or dry vegetables contaminated with mycotoxins.

11 Claims, No Drawings

PROCESS FOR TREATING STORAGE RESERVOIRS CONTAMINATED WITH MYCOTOXINS

The present invention relates to the use of eugenol or of clove oil for the treatment of reservoirs for storing dry fruits, dry vegetables, cereals or oil-producing plants, contaminated with mycotoxins and/or the fungi or moulds that produce them.

On a worldwide scale, approximately 25% of food products are contaminated with mycotoxins. Mycotoxins are highly toxic, sometimes carcinogenic, molecules produced by certain fungi which contaminate foods.

There are about ten or so mycotoxins which commonly contaminate food products and which are dangerous to humans and/or animals.

The most well-known today are aflatoxins, ochratoxins, toxins from *Fusarium*, such as zearalenone, trichothecenes and fumonisins, or patulin.

The starting materials are contaminated in the field or during storage under certain conditions of temperature and moisture, growing conditions, strains present, etc.

The fungi responsible are certain parasitic fungi or moulds, such as *Fusarium, Penicillium* and *Aspergillus*. Dry fruits, dry vegetables, cereals or oil-producing plants are the most commonly contaminated products.

Mycotoxins, which are very resistant, are found in the finished products; they are destroyed neither by cold nor by heat; they are stable during various conversion processes.

Cases of acute poisoning in humans have been known since the Middle Ages. Acute poisoning in humans in industrial countries is now rare, but there is a not insignificant risk of developing damage, in particular to the liver and kidneys, or cancers, related to the regular ingestion of low doses.

When these mycotoxins are consumed by livestock animals, they can be found in the meat (in particular in the muscles and offal) and the milk, either in unmodified form, or converted into compounds that are sometimes more toxic than the initial mycotoxin.

Cases of poisoning are recorded in livestock colonies, such as fertility problems due to zearalenone, animals not eating due to deoxynivalenol, or else acute kidney toxicity due to ochratoxin A. The development of mycotoxins, which are impossible to eliminate from food once produced, can therefore lead to problems all along the food chain, with serious economic repercussions.

It is therefore essential to provide compositions that make it possible to prevent contamination with these mycotoxins.

Moreover, for the specific decontamination of food products, it is important for these compositions to be non-toxic and nutritionally acceptable.

Eugenol is a terpene derived from clove oil. The use of a composition containing eugenol for the treatment of fruit and vegetables after harvest for the purpose of extending their storage life has been described in application FR 98 08 995. The process described comprises the application of said composition to the fruit and vegetables.

Moreover, a process for inhibiting the sprouting of potatoes using eugenol has been described in application FR 98 15 305. The process comprises the application of the composition to the potatoes by immersion or sprinkling or by thermal fogging.

However, the potential use of eugenol for the treatment of reservoirs for storing dry fruit, dry vegetables, cereals or oil-producing plants contaminated with the mycotoxins and/or the fungi or moulds that produce them has, to date, been neither described nor suggested.

The present inventors have thus demonstrated that storage reservoirs, such as cereal silos, are highly polluted with fungi or moulds such as *Penicillium, Aspergillus* or *Fusarium*, producers of mycotoxins. This contamination persists even when the silos are empty, such that the new harvests are again contaminated.

If is therefore important to be able to decontaminate these silos. However, given the size of these reservoirs (up to several hundred tonnes), an extremely powerful active agent is necessary. Silo decontamination is also particularly difficult in that the walls are porous and the mycotoxins and/or moulds or fungi that produce them can lodge themselves therein and withstand simple decontamination of the ambient air. It is therefore necessary to provide an extremely effective process for applying the active agent even in the porosities of the walls.

Now, no easy, relatively inexpensive and effective decontamination method has been developed up until now.

The present inventors have now discovered, and it is one of the subjects of the present invention, that eugenol or clove oil exhibits, entirely unexpectedly, an activity which allows the treatment of storage reservoirs for dry fruit, dry vegetables, cereals or oil-producing plants contaminated with mycotoxins and/or the fungi or moulds that produce them.

Moreover, since eugenol is a product of natural origin, it is most particularly suitable for the decontamination of food products.

The present invention therefore relates to a process for decontaminating or preventing the contamination, with mycotoxins and/or fungi or moulds that produce them, of reservoirs for storing dry fruit, dry vegetables, cereals or oil-producing plants, comprising the application, to said reservoirs in which the dry fruit, dry vegetables, cereals or oil-producing plants are stored or intended to be stored, of a composition comprising eugenol, isoeugenol, one of their nutritionally acceptable salts and/or clove oil, or mixtures thereof.

Preferably, said mycotoxins are selected from ochratoxin A, deoxynivalenol, aflatoxins (B1, B2, G1, G2, M1, M2), zearalenone, trichothecenes (DAS, toxin D2, nivalenol, fusarenone X), fumosinins (B1 and B2), citrinin, penicillic acid, vomitoxin and patulin; more particularly, ochratoxin A.

According to another aspect of the present invention, said mycotoxins are produced by fungi of the *Fusarium, Penicillium* and *Aspergillus* genera.

The production of moulds by these genera may be species-dependent or may be expressed under certain conditions.

More particularly, *Penicillia* and *Aspergilli* generally develop in storage reservoirs for dry fruit, dry vegetables, cereals or oil-producing plants. Among the *Penicillia*, mention may be made of *Penicillium verrucosum*, which can produce ochratoxin A and/or citrinin, *Penicillium orantiogriseum* which produces penicillic acid and/or ochratoxin A, and *Penicillium citrinum* and *expansum* which produce citrinin and/or patulin. Among the *Aspergilli*, mention may be made of *Aspergillus ochraceus, Aspergillus carbonarius* and *Aspergillus niger* which produce ochratoxin A.

More particularly, the *Fusaria* contaminate plants, more principally wheat plants.

Among the cereals for implementing the process according to the invention, mention may be made of wheat, maize, rice and barley.

Among the oil-producing plants, mention may be of sunflower, rapeseed and groundnut.

The cereals or oil-producing plants can be in the form of grains, germs, seeds or plants.

Among the dry fruit and dry vegetables, mention may be made of grapes, coffee, cacao, beans and lentils.

Cereals and oil-producing plants are in particular preferred.

The composition according to the invention can be applied by sprinkling or thermal fogging. Application by thermal fogging is in particular preferred.

According to a particularly advantageous aspect, the process according to the invention is carried out for decontaminating or preventing the contamination of silos; preferably, the composition is applied to the reservoirs before filling with the dry fruit, dry vegetables, cereals or oil-producing plants, or once the silo has been filled or partially filled, or else simultaneously while said silo is being filled with said dry fruit, dry vegetables, cereals or oil-producing plants.

According to a particularly preferred aspect, the composition is applied to an empty silo.

According to the invention, the expression "composition comprising eugenol, isoeugenol or clove oil" is intended to mean these ingredients in pure form or any diluted composition comprising these ingredients. Thus, the composition for the process according to the invention comprises, as percentage by weight:
 from 15% to 100% of said active ingredient;
 from 0% to 10% of one or more agents for reducing the evaporation of the active ingredient;
 from 0% to 85% of a surfactant selected from anionic surfactants and non-ionic surfactants, and mixtures thereof; and
 from 0% to 80% of a solvent selected from water, ($C_1$-$C_6$) alkanols, ($C_2$-$C_6$)alkylene glycol, poly($C_1$-$C_6$)alkylene glycol, ($C_1$-$C_6$) alkyl esters of ($C_1$-$C_6$)alkanoic acids, and mixtures thereof.

More preferably, pure eugenol or pure clove oil, which generally comprises approximately 85% of eugenol, is used.

Alternatively, the following composition can also be used:
 from 15% to 60% of active ingredient;
 from 1% to 8% of one or more agents for reducing evaporation;
 from 25% to 60% of a surfactant; and
 from 0% to 30% of said solvent.

More specifically, the following formulation A can be used:
 eugenol: 30%;
 dipropylene glycol (DPG): 50%;
 surfactants: 5%
 water: 15%.

One of the advantages associated with these compositions is their high content of active ingredient.

In the text above and hereinafter, the percentages are by weight/volume relative to the total volume of the composition.

The formulation of the treating composition depends on its method of application.

The agents for reducing evaporation of the active ingredient are known in the art and can in particular be selected from water-dispersible polyterpenes, glycerol esters of pine resin, gum lacquers, lecithins, drying oils, polyvinyl alcohol, polyvinylpyrrolidone, alkali metal polyacrylates and gum arabic.

The various surfactants or emulsifiers are known per se.

According to the present invention, the term "emulsifier" is intended to mean any type of agent normally used for this purpose, such as ethoxylated fatty alcohols, ethoxylated fatty acids, ethoxylated alkylphenols or any other non-ionic product.

The surfactants preferably used in the context of the invention are anionic or non-ionic surfactants.

Examples of non-ionic surfactants that can be used according to the invention are, in particular:
 the product of condensation of an aliphatic fatty alcohol, which is preferably $C_8$-$C_{22}$, with a $C_2$-$C_3$ alkylene oxide. The $C_2$-$C_3$ alkylene oxide can be ethylene oxide, propylene oxide or a mixture of ethylene oxide and propylene oxide in any proportions. An example of such surfactants is the product of condensation of lauryl alcohol (or n-dodecyl alcohol) with 30 mol of ethylene oxide;
 the product of condensation of an alkylphenol in which the alkyl chain is $C_8$-$C_{22}$, with a $C_2$-$C_3$ alkylene oxide. In this case also, the products of condensation with ethylene oxide, propylene oxide or a mixture of ethylene oxide and propylene oxide in any proportions are also advantageous. By way of example of such surfactants, mention may be made of the product of condensation of n-nonylphenol with 10 mol of ethylene oxide;
 the product of condensation of a fatty acid, which is preferably $C_8$-$C_{22}$, with a $C_2$-$C_3$ alkylene oxide, for example ethylene oxide or propylene oxide or a mixture of ethylene oxide and propylene oxide in any proportions. These condensation products have an alkoxylated chain on the hydroxyl function of the carboxylic group. Preferred surfactants of this group are the condensation products obtained from ricinoleic acid with 10 mol of ethylene oxide.

Examples of anionic surfactants that can be used according to the invention are, in particular:
 water-soluble salts of long-chain alkyl sulphates, and in particular water-soluble salts of ($C_8$-$C_{24}$)alkyl sulphates, such as alkali metal lauryl sulphates, and more particularly sodium lauryl sulphate; and
 water-soluble salts of alkylaryl sulphonates, and in particular water-soluble salts of ($C_8$-$C_{24}$)alkyl($C_6$-$C_{10}$)aryl sulphonates, such as alkali metal dodecyl-benzene sulphonates, and more particularly sodium dodecylbenzene sulphonate.

The invention is not, however, limited to the use of these specific surfactants.

The solvents that may be used in the treating composition are in particular selected from $C_1$-$C_{12}$ aliphatic alcohols, glycols and alkyl esters of carboxylic acids.

More specifically, in the context of the invention, the glycols denote alkylene glycols and polyalkylene glycols.

The term "alkylene glycol" is intended to mean dihydroxylated alcohols derived from aliphatic hydrocarbons by replacement of two hydrogen atoms with two hydroxyl groups. ($C_2$-$C_6$)Alkylene glycol such as ethylene glycol and propylene glycol are preferred.

The term "polyalkylene glycol" is intended to mean the compounds of formula

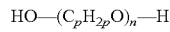

where p and n are integers between 2 and 6.

By way of example, mention may be made of dipropylene glycol.

According to the invention, the $C_pH_{2p}O$ group is linear or branched. The polyalkylene glycol that is preferred according to the invention is dipropylene glycol.

The preferred alkyl esters of carboxylic acids are the ($C_1$-$C_6$)alkyl esters of a ($C_1$-$C_6$)alkanoic acid, such as butyl acetate.

When the treating composition comprises a nutritionally acceptable salt, the latter can be introduced into the composition as it is prepared, in the form of a salt or in neutral form. In the latter case, the salt is formed in situ by addition of an appropriate base, such as an alkali metal hydroxide (sodium hydroxide or potassium hydroxide).

The amount of the solution according to the invention that must be applied depends essentially on the method of application selected. More generally, the amount of active ingredient applied is adjusted according to the duration of storage.

The treating compositions are prepared in a manner that is conventional in itself, by simply mixing the constituents thereof, optionally with stirring.

The compositions according to the invention should be applied one or more times. According to an advantageous aspect, a treatment is carried out in the silo, preferably before filling, or on the dry fruit, dry vegetables, cereals or oil-producing plants immediately after harvesting.

The amount of treating composition that must be applied depends on the nature of the dry fruit, dry vegetables, cereals or oil-producing plants concerned and on the method of application selected. Generally, between 1 and 200 $cm^3$ per $m^3$ of storage is applied, preferably between 10 and 100 $cm^3/m^3$, it being understood that these doses are related to pure eugenol.

The composition can in particular be applied by sprinkling or thermal fogging. Application by thermal fogging is more particularly preferred. The solution is then applied at a temperature of between 150° C. and 250° C., depending on the nature of the composition. Thus, when pure eugenol is applied, the temperature is preferably approximately 230° C. When the composition A is applied, the thermal fogging is preferably carried out at approximately 180° C. This technique is known in itself and is described in FR 98 015305 and FR 99 04534.

Thermal fogging is a process consisting in applying an extremely fine fog (in which the droplets are of the order of a micrometer in size), which is produced by injection of a liquid into a stream of hot air, which serves as a carrier for said treating composition. The fog thus produced allows a homogeneous application.

The thermal fogging may advantageously be carried out using a thermal fogging device as described in FR 87 04 960 or sold under the name Electrofog Xeda®. This electric thermal fogging machine consists of a high-pressure fan, an electrical resistor and a volumetric pump which ensures strict regularity of the characteristics of the fog produced and a very gradual introduction of the treating composition into the storage chamber.

Conventionally, the conditions for obtaining a droplet size of 0.5 to 10 microns, in particular of the order of one micron, which are characteristic of a fog produced by thermal fogging, comprise heating the air to a temperature of 400° C. to 650° C. before injecting the liquid.

According to the invention, the temperature of the fog leaving the thermal fogging device is advantageously selected between 110° and 300° C., preferably between 150° and 260° C., for example between 170° and 250° C.

This variant is more specifically described in application FR 94 15 329.

Generally, the thermal fogging in the silos is carried out by placing the thermal fogging device in the silo chamber, preferably in the upper half of the silo, for example by placing the thermal fogging device on a platform placed at the top of the chamber.

The application may be continuous or intermittent over the course of the storage period.

Preferably, the application is carried out in the storage chamber before filling, or repeated approximately every two months.

The following examples are given by way of non-limiting illustration of the present invention.

EXAMPLE 1

Protocol

1. Prior Characterization of the Natural Contamination of Empty Cells of a Seed Station (Nogent-sur-Seine)

Six cells (noted '20', 'L', '12', 'F', '8' and 'I') were studied. These are concrete cells with a conical bottom (bottom for completely emptying the cell and eliminating more readily the debris and dust before ensilaging the next harvest). The cells identified by a number have a capacity of 350 t, those identified by a letter have a capacity of 50 t. The level of contamination of the six cells was evaluated by trapping the contaminated spores or particles using an Airtest introduced into the cell via an access hatch located at the base of the cell.

The Petri dishes 90 mm in diameter, placed in the Airtest and constituting the trap, contained a Malt Agar+Triton medium; the addition of triton modifies the development of the fungal colonies, which remain compact and are easy to count. The volume of air passing through the Airtest was set at 100 l, except for one cell in which we tested 4 different volumes of air (10 l, 20 l, 40 l, 100 l). For each mode, three repetitions (3 Petri dishes) were carried out.

Two types of trapping were carried out; atmospheric trapping and trapping on the storage cells. In fact, these walls have rough patches and can retain mould spores or infected particles. The Airtest was placed approximately 5 mm from the wall.

To evaluate the level of contamination of the grain storage cells, a comparison with an outside contamination control (4 repetitions) was carried out by atmospheric trapping outside the silo (approximately 50 m from the silo buildings).

2. Study on Two Empty Cells Before and after Treatment with Eugenol

Atmospheric trapping procedures and trapping procedures on the walls were carried out on two cells for which the level of natural contamination was shown to be sufficient in study 1, just before and 10 days after treatment by thermal fogging with eugenol. Five repetitions were carried out (5 Petri dishes) for each mode.

The eugenol thermal fogging treatment was carried out on a platform on which the thermal fogging device was installed. After thermal fogging, the cells remained closed for 10 days in order to ensure that the treatment was highly effective.

Given the difficulty in handling Petri dishes in an environment as contaminated as a silo, an additional control ("handling control") was carried out. Four repetitions (4 Petri dishes) were carried out for this control.

Results

1. Prior Characterization of the Natural Contamination of Six Empty Cells

The six cells studied show a very high level of contamination with *Penicillium* spp. A contamination with mould of the *Aspergillus* genus is noted in cell 12. On average, respectively 77 and 85 *Aspergillus* spp. develop on the Petri dishes derived from the atmosphere and the walls of cell 12, whereas, most commonly, none and at most 17 are revealed in the other cells (Table 1). This contamination, although much lower than the contamination with *Penicillium* spp., cannot be ignored since *Aspergillus* spp. are also potential ochratoxin A producers.

The comparison of the *Penicillium* spp. contamination of the empty cells with that of the outside control is striking (Table 1). On average, only 1.25 colonies of *Penicillium* spp. and no colonies of *Aspergillus* spp. are revealed. It is essentially colonies of *Cladosporium* spp. type which develop from the outside atmospheric trapping.

Even though the degree of *Penicillium* spp. contamination is very high for the six cells, the cells L and F appear to be even more contaminated than the others, in particular on their walls (Table 1). In general, the trapping on the walls gave more *Penicillium* spp. colonies than the atmospheric trapping, except for cell 8. The walls of the storage cells therefore constitute an important source of contamination.

TABLE 1

Estimation of the average number of colonies per Petri dish, obtained after atmospheric trapping and trapping on the walls of 6 empty storage cells

| Cell | Grain stored | Airtest volume | Penicillium Atmospheric contamination | Penicillium Wall contamination | Aspergillus Atmospheric contamination | Aspergillus Wall contamination |
|---|---|---|---|---|---|---|
| 20 | wheat | 100 l | 1560 | 3210 | 0 | 0 |
| L | wheat | 100 l | 2650 | 7500 | 0 | 0 |
| 12 | wheat | 100 l | 1240 | 1860 | 77 | 85 |
| F | barley | 100 l | 2150 | 6480 | 3 | 0 |
| 8 | barley | 100 l | 2020 | 1270 | 17 | 0 |
| I | barley | 100 l | 3250 | 5900 | 0 | 0 |
| Outside control* | | 100 l | 1.25 | | 0 | |

*Atmospheric trapping carried out outside the silo buildings.

Other fungi (*Cladosporium* spp.) and bacteria and yeasts also contaminate these cells, but to a lesser degree than *Penicillium* spp. The effect of increasing air volumes circulating in the Airtest on the number of trapped colonies, was studied in cell I (Table 2).

TABLE 2

Estimation of the average number of colonies per Petri dish obtained after trapping with various volumes of the Airtest in cell I

| Airtest volume | Penicillium Atmospheric contamination | Penicillium Wall contamination |
|---|---|---|
| 10 l | 2140 | 1190 |
| 20 l | 2680 | 2910 |
| 40 l | 2530 | 3640 |
| 100 l | 3250 | 5900 |

Study 1 showed that the level of *Penicillium* spp. contamination of these six cells is extremely high and makes it possible to readily test the effect of a treatment of the cells. This is the object of Study 2, for which cell L was selected, because of its extreme level of contamination, and cell 12 was selected because of the presence of another genus of mould, *Aspergillus* spp.

2. Study of Cells L and 12 Before and after Treatment 4 l and 20 l of eugenol, respectively, were subjected to thermal fogging at 230° C. (for approximately ¾ h) in cell L ($\approx$50 m$^3$) and in cell 12 ($\approx$350 m$^3$).

The evaluation of the contamination after treatment reveals a clear decrease in the level of *Penicillium* spp. contamination with the treatment in the 2 cells (Table 3).

The *Aspergillus* spp. contamination in cell 12 is completely controlled by the treatment.

TABLE 3

Summary of the effect of the treatment by thermal fogging with eugenol on the atmospheric contamination and the wall contamination of two empty cells

| Cell | History | Type of trapping (Airtest) | Volume of air(l) Airtest | Penicillium contamination (number colonies/Petri dish) Before treatment | Penicillium contamination (number colonies/Petri dish) After treatment | Aspergillus contamination (number colonies/Petri dish) Before treatment | Aspergillus contamination (number colonies/Petri dish) After treatment |
|---|---|---|---|---|---|---|---|
| L | wheat | Atmosphere | 100 | 2650 | 106 | 0 | 0 |
|   |       | Wall       | 100 | 7500 | 85  | 0 | 0 |
| 12 | wheat | Atmosphere | 100 | 1240 | 400 | 77 | 0 |
|   |       | Wall       | 100 | 1860 | 207 | 85 | 0 |

It should be noted that the active substance can accumulate in the bottom of the cell. This is entirely advantageous since the dust and the small pieces of debris, still present in the storage cells and an important source of contamination, also accumulate there. They can thus be effectively treated.

CONCLUSION

The above results demonstrate that the process for thermal fogging of eugenol in the cells is found to be very effective against moulds that potentially produce ochratoxin A, which are *Penicillium* spp. and *Aspergillus* spp., present in the grain storage cells. The effectiveness relates both to the atmospheric contamination and the wall contamination in the cells.

The invention claimed is:

1. A process for decontaminating mycotoxins and/or the fungi or moulds that produce them, in a silo for storing cereals, dry fruit, dry vegetables or oil-producing plants, comprising the steps of:
    decontaminating an empty silo comprising applying, by thermal fogging, to an empty silo before storage, a composition comprising, as an active ingredient, eugenol, isoeugenol, clove oil or one of their nutritionally acceptable salts, or mixtures thereof, to treat the empty silo, and
    filling of said treated silo with contaminated cereals, dry fruit, dry vegetables or oil-producing plants so that said contaminated cereals, dry fruit, dry vegetables or oil-producing plants are decontaminated when stored within said treated silo.

2. The process according to claim 1, wherein the eugenol, the isoeugenol, the clove oil or one of their nutritionally acceptable salts, or mixtures thereof, is applied at a dose of between 1 and 200 cm$^3$ per m$^3$ of storage.

3. The process according to claim 1, wherein said mycotoxins are selected from the group consisting of ochratoxin A, deoxynivalenol, aflatoxins, zearalenone, trichothecenes, fumosinin, citrinin, penicillic acid, vomitoxin, and patulin.

4. The process according to claim 1, for which said mycotoxins are selected from ochratoxin A.

5. The process according to claim 1, in which said composition comprises, as percentage. by weight:

from 15% to 100% of said active ingredient;

from 0% to 10% of one or more agents for reducing the evaporation of the active ingredient;

from 0% to 85% of a surfactant selected from anionic surfactants and non-ionic surfactants, and mixtures thereof; and from 0% to 80% of a solvent selected from water, (C1-C6) alkanols, (C2-C6)alkylene glycol, poly(C1-C6)alkylene glycol, (C1-C6)alkyl esters of (C1-C6)alkanoic acids, and mixtures thereof.

6. The process according to claim 1, in which said composition is pure eugenol or pure clove oil.

7. The process according to claim 1, in which said silo is contaminated or presents a risk of contamination with *Penicillium* or *Aspergillus*.

8. The process according to claim 1, in which the cereal is selected from wheat, maize, rice and barley.

9. The process according to claim 8, in which the cereal is wheat.

10. The process according to claim 1, in which the oil-producing plant is selected from sunflower, rapeseed and groundnut.

11. The process according to claim 1, for which said cereals or oil-producing plants are in the form of grains, plants, seed or germs.

\* \* \* \* \*